(12) United States Patent
Doll et al.

(10) Patent No.: US 7,608,643 B2
(45) Date of Patent: *Oct. 27, 2009

(54) COMPOUNDS FOR INHIBITING KSP KINESIN ACTIVITY

(75) Inventors: Ronald J. Doll, Convent Station, NJ (US); Ronald Herbst, Palo Alto, CA (US); Wolfgang Seghezzi, Mountain View, CA (US); Emma M. Lees, Oakland, CA (US); William F. Estacio, San Lorenzo, CA (US)

(73) Assignee: Schering Corporation, Kenilworth, NJ (US)

( * ) Notice: Subject to any disclaimer, the term of this patent is extended or adjusted under 35 U.S.C. 154(b) by 150 days.

This patent is subject to a terminal disclaimer.

(21) Appl. No.: 11/370,005

(22) Filed: Mar. 7, 2006

(65) Prior Publication Data

US 2006/0258699 A1 Nov. 16, 2006

Related U.S. Application Data

(60) Provisional application No. 60/659,973, filed on Mar. 9, 2005.

(51) Int. Cl.
*A01N 35/04* (2006.01)
*A61K 31/541* (2006.01)
*A01N 43/90* (2006.01)
*A61K 31/519* (2006.01)
*A61K 31/12* (2006.01)
*C07D 419/04* (2006.01)
*C07D 417/00* (2006.01)

(52) U.S. Cl. .................. 514/683; 544/279; 544/284; 514/292; 514/260.1; 514/264.1; 514/265.1; 514/290; 546/83

(58) Field of Classification Search .......... 514/292, 514/683, 260, 265, 264; 546/83; 544/278, 544/279
See application file for complete search history.

(56) References Cited

FOREIGN PATENT DOCUMENTS

| DE | 26 38 828 | 3/1978 |
|---|---|---|
| WO | WO 02/28837 | 4/2002 |
| WO | WO 03/040096 | 5/2003 |
| WO | WO 03/050064 | 6/2003 |
| WO | WO 03/055878 | 7/2003 |
| WO | WO 2004/022523 | 3/2004 |
| WO | WO 2004/111058 | 12/2004 |

OTHER PUBLICATIONS

Morissette et al, High-throughput cyrstallization: polymorphs, salts, co-crystals and solvates of pharmeceutical solids, Advance drug delivery Reviews 56 (2004) 275-300.*
Vippagunta et al, Crystalline solids, Advanced Drug Delivery Reviews vol. 48, Issue 1, May 16, 2001, pp. 3-26.*

Cox, et al.: Kinesin spindle protein (KSP) Inhibitors. Part 1: "The discovery of 3,5-diaryl-4,5-dihydropyrazoles as potent and selective inhibitors of the mitotic kinesin KSP" Bioorganic & Medicinal Chemistry Letters, 2005, vol. 15, pp. 2041-2045.

Dabaeva et al.: "Synthesis of dihydro-10H-pyrano[3',4':5,6]pyrido[3,2:4",5"]-thieno[3",2"-d][3,1]oxazines and pyrimidines", Chemistry of Heterocyclic Compounds (1995), pp. 219-222, vol. 31, No. 2. XP009069920.

Dotsenko et al.: Synthesis of condenses sulfur-containing heterocycles based on partly hydrogenated pyridines. Database CAPLUS [online] Chemical Abstracts Service, Columbus, Ohio (2004), 3 pgs. XP002392884.

El-Dean et al.: "Synthesis of Some Thienotetrahydroquinoline Derivatives", Journal of the Chinese Chemical Society (2004), pp. 335-345, vol. 51, No. 2. XP009069921.

Fathy, N.M. et al.: "Synthesis of some thienoquinoline derivatives with expected pharmacological activity." Egyptian Journal of Pharmaceutical Sciences, 1990, vol. 31, pp. 375-383 (abstract only).

Federov et al.; "Reactions of (S)-N-trifluoroacetyl-5-bromo-4-oxonorvaline methyl ester with vicinal mercaptonitriles. Synthesis of delta-hetaryl-substituted alpha-amino acids" Russian Chemical Bulletin (2003), pp. 2063-2069, vol. 52, No. 9. XP002392838.

Gnanasekaran et al.: "Thienoquinolines; Part VIII. A three-step synthesis of thieno[2,3-b]quinolines from anilines", Synthesis (1977), pp. 612-614, vol. 9. XP002387124.

Hull, Roy: "Reactions of heterocycles with thiophosgene. Part II. Then chemistry of 3-formylquinoline-2(1H)-thione" Journal of the Chemical Society, Perkin Transactions 1 (1973), pp. 2911-2914, vol. 23. XP008065720.

Ibrahim et al.: "Intramolecular 4+2 cycloaddition of thieno[2,3-e][1,2,4]triazines: routes towards condensed thieno[2,3-b]pyridines". Tetrahedron (Oct. 20, 2003), pp. 8489-8498, vol. 59, No. 43. XP004463728.

Kim, et al.: Synthesis and SAR of pyrrolotriazine-4-one based Eg5 inhibitors. Bioorganic & Medicinal Chemistry Letters, 2006, vol. 16, pp. 3937-3942.

(Continued)

*Primary Examiner*—Ardin Marschel
*Assistant Examiner*—Savitha Rao
(74) *Attorney, Agent, or Firm*—Keith D. MacMillan; Krishna G. Banerjee

(57) ABSTRACT

The present invention relates to compounds of Formula I or pharmaceutically acceptable salts or solvates thereof:

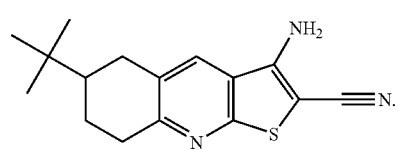

The present invention provides compositions comprising these compounds that are useful for treating cellular proliferative diseases or disorders associated with KSP kinesin activity and for inhibiting KSP kinesin activity.

7 Claims, No Drawings

OTHER PUBLICATIONS

Klemm et al.: "Chemistry of thienopyridines. XXXVII. Syntheses in the Cyclopenta, Cyclohexa-, and cycloheptathieno[2,3-b]pyridine Series. Three analogs of 9-amino-1,2,3,4-tetrahydroacridine [1]", Journal of Heterocyclic Chemistry (1990), pp. 1537-1541, vol. 27, No. 6. XP002392839.

Meth-Cohn, Otto: "A versatile new synthesis of quinolines and related fused pyridines. Part 9. Synthetic application of the 2-chloroquinoline-3-carboxaldehydes." Journal of the Chemical Society, Perkin, Transactions 1 1981, pp. 2509-2517 (abstract only).

Nithyadevi, V. et al: "Synthesis of thieno(2,3-b)quinoline-2-carboxylic esters from 3-(2-oxo-1,2-dihydro-3-quinolyl)acrylic esters." Heterocyclic Communications, 2004, vol. 10, pp. 339-342 (abstract).

Nithyadevi, V. et al: "Synthesis and spectral studies of thieno(2,3-b)quinoline derivatives", Asian Journal of Chemistry 2004, vol. 16, pp. 3-4 XP008065724.

Rodinovskaya et al.: "Regioselective synthesis of 5,6-polymethylene-3-cyanopyridine-2(1H)-thiones and fused heterocycles based on them":, Russian Chemical Bulletin (1994), pp. 449-457, vol. 43, No. 3. XP009069913.

Rodinovskaya et al.: "Synthesis of substituted 4-hydroxy-1H-thieno[2,3-b;4,5-b']dipyridin-2-ones": Russian Chemical Bulletin (2000), pp. 348-354, vol. 49, No. 2. XP009070162.

Sunder-Plassman, et al.: "Synthesis and biological evaluation of new tetrahydro-b-carbolines as inhibitors of the mitotic kinesin Eg5", Bioorganic & Medicinal Chemistry 2005, pp. 6094-6111.

Suzuki et al.: "Synthesis of Antimicrobial Agents.III. Synthesis and Antimicrobial Activities of Thiazolo[5,4-b]naphthyridine Derivatives", Chem. Pharm. Bull. (1979), pp. 410-418, vol. 27, No. 2. XP001247411.

Tarby, et al.: "Inhibitors of human mitotic kinesin Eg5: characterization of the 4-phenyl-tetrahydroisoquinoline lead series", Bioorganic & Medicinal Chemistry Letters 2006, vol. 16, pp. 2095-2100.

International Search Report for International Application No. PCT/US2006/008150, mailed Jul. 12, 2006—5pgs.

International Search Report for International Application No. PCT/US2006/008145, mailed Sep. 28, 2006-13 6pgs.

* cited by examiner

COMPOUNDS FOR INHIBITING KSP KINESIN ACTIVITY

This Application claims the benefit of U.S. Provisional Application Ser. No. 60/659,973, filed Mar. 9, 2005, which is incorporated herein by reference in its entirety.

FIELD OF THE INVENTION

The present invention relates to compound and compositions that are useful for treating cellular proliferative diseases or disorders associated with Kinesin Spindle Protein ("KSP") kinesin activity and for inhibiting KSP kinesin activity.

BACKGROUND OF THE INVENTION

Cancer is a leading cause of death in the United States and throughout the world. Cancer cells are often characterized by constitutive proliferative signals, defects in cell cycle checkpoints, as well as defects in apoptotic pathways. There is a great need for the development of new chemotherapeutic drugs that can block cell proliferation and enhance apoptosis of tumor cells.

Conventional therapeutic agents used to treat cancer include taxanes and vinca alkaloids, which target microtubules. Microtubules are an integral structural element of the mitotic spindle, which is responsible for the distribution of the duplicated sister chromatids to each of the daughter cells that result from cell division. Disruption of microtubules or interference with microtubule dynamics can inhibit cell division and induce apoptosis.

However, microtubules are also important structural elements in non-proliferative cells. For example, they are required for organelle and vesicle transport within the cell or along axons. Since microtubule-targeted drugs do not discriminate between these different structures, they can have undesirable side effects that limit usefulness and dosage. There is a need for chemotherapeutic agents with improved specificity to avoid side effects and improve efficacy.

Microtubules rely on two classes of motor proteins, the kinesins and dyneins, for their function. Kinesins are motor proteins that generate motion along microtubules. They are characterized by a conserved motor domain, which is approximately 320 amino acids in length. The motor domain binds and hydrolyses ATP as an energy source to drive directional movement of cellular cargo along microtubules and also contains the microtubule binding interface (Mandelkow and Mandelkow, Trends Cell Biol. 2002, 12:585-591).

Kinesins exhibit a high degree of functional diversity, and several kinesins are specifically required during mitosis and cell division. Different mitotic kinesins are involved in all aspects of mitosis, including the formation of a bipolar spindle, spindle dynamics, and chromosome movement. Thus, interference with the function of mitotic kinesins can disrupt normal mitosis and block cell division. Specifically, the mitotic kinesin KSP (also termed EG5), which is required for centrosome separation, was shown to have an essential function during mitosis. Cells in which KSP function is inhibited arrest in mitosis with unseparated centrosomes (Blangy et al., Cell 1995, 83:1159-1169). This leads to the formation of a monoastral array of microtubules, at the end of which the duplicated chromatids are attached in a rosette-like configuration. Further, this mitotic arrest leads to growth inhibition of tumor cells (Kaiser et al., J. Biol. Chem. 1999, 274:18925-18931). Inhibitors of KSP would be desirable for the treatment of proliferative diseases, such as cancer.

Kinesin inhibitors are known, and several molecules have recently been described in the literature. For example, adociasulfate-2 inhibits the microtubule-stimulated ATPase activity of several kinesins, including CENP-E (Sakowicz et al., Science 1998, 280:292-295). Rose Bengal lactone, another non-selective inhibitor, interferes with kinesin function by blocking the microtubule binding site (Hopkins et al, Biochemistry (2000) 39:2805-2814). Monastrol, a compound that has been isolated using a phenotypic screen, is a selective inhibitor of the KSP motor domain (Mayer et al., Science 1999, 286:971-974). Treatment of cells with monastrol arrests cells in mitosis with monopolar spindles.

KSP, as well as other mitotic kinesins, are attractive targets for the discovery of novel chemotherapeutics with anti-proliferative activity. There is a need for compounds useful in the inhibition of KSP, and in the treatment of proliferative diseases, such as cancer.

SUMMARY OF THE INVENTION

The present invention relates to a compound represented by Formula I:

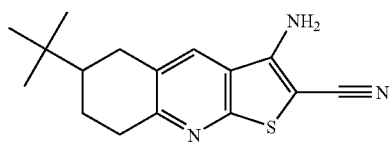

I or a salt or solvate thereof.

In one embodiment, the present invention provides a pharmaceutical formulation or a composition comprising the above compound or a salt or solvate thereof and a pharmaceutically acceptable carrier, adjuvant or vehicle. In another embodiment, methods for the treatment of cellular proliferative diseases, disorders associated with KSP kinesin activity and/or for inhibiting KSP kinesin activity in a subject comprising administering a therapeutically effective amount of the above compound and a pharmaceutically acceptable carrier, adjuvant or vehicle to the subject are also provided.

Other than in the operating examples, or where otherwise indicated, all numbers expressing quantities of ingredients, reaction conditions, and so forth used in the specification and claims are to be understood as being modified in all instances by the term "about."

DETAILED DESCRIPTION

In one embodiment, the present invention relates to relates to a compound represented by Formula I:

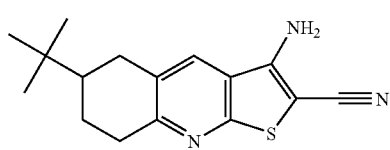

I or a pharmaceutically acceptable salt or solvate thereof.

In other embodiments, the present invention provides processes for producing the inventive compound, pharmaceutical formulations or compositions comprising the compound, and methods of treating or preventing one or more conditions or diseases associated with KSP kinesin activity such as those discussed in detail below.

As used above, and throughout the specification, the following terms, unless otherwise indicated, shall be understood to have the following meanings:

"Subject" includes both mammals and non-mammalian animals.

"Mammal" includes humans and other mammalian animals.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties. It should be noted that any atom with unsatisfied valences in the text, schemes, examples and tables herein is assumed to have the hydrogen atom(s) to satisfy the valences.

Also included in the scope of this invention are oxidized forms of the heteroatoms (e.g., nitrogen and sulfur) that are present in the compound of this invention. Such oxidized forms include $N(O)$ $[N^+—O^-]$, $S(O)$ and $S(O)_2$.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

As used herein, the term "composition" is intended to encompass a product comprising the specified ingredients in the specified amounts, as well as any product which results, directly or indirectly, from combination of the specified ingredients in the specified amounts.

Isomers of the compound of Formula I, including enantiomers, stereoisomers, rotamers, tautomers, diastereomers, and racemates are also contemplated as being part of this invention. The invention includes d and l isomers in both pure form and in admixture, including racemic mixtures. Isomers can be prepared using conventional techniques, either by reacting optically pure or optically enriched starting materials or by separating isomers of the compound of the Formula I. Isomers may also include geometric isomers, e.g., when a double bond is present. Polymorphous forms of the compound of Formula I, whether crystalline or amorphous, also are contemplated as being part of this invention. The (+) isomer of the present compound are preferred.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C—$ or $^{14}C$-enriched carbon are also within the scope of this invention.

It will be apparent to one skilled in the art that certain compounds of this invention may exist in alternative tautomeric forms. All such tautomeric forms of the present compounds are within the scope of the invention. Unless otherwise indicated, the representation of either tautomer is meant to include the other. For example, both isomers (1) and (2) are contemplated:

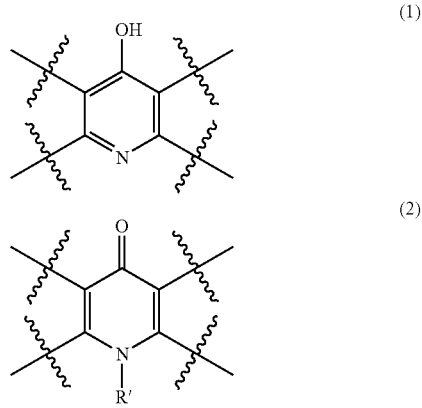

wherein R' is H or $C_{1-6}$ unsubstituted alkyl.

Prodrugs and solvates of the compound of the invention are also contemplated herein. The term "prodrug", as employed herein, denotes a compound that is a drug precursor which, upon administration to a subject, undergoes chemical conversion by metabolic or chemical processes to yield the compound of formula I or a salt or solvate thereof (e.g., a prodrug on being brought to the physiological pH or through enzyme action is converted to the desired drug form). A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compound of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving a compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of a compound or a composition of the present invention effective in inhibiting mitotic kinesins, in particular KSP kinesin activity, and thus producing the desired therapeutic, ameliorative, inhibitory or preventative effect in a suitable subject.

The compound of formula I can form salts which are also within the scope of this invention. Reference to the compound of formula I herein is understood to include reference to salts, and solvates thereof, unless otherwise indicated. The term "salt(s)", as employed herein, denotes acidic salts formed with inorganic and/or organic acids, as well as basic salts formed with inorganic and/or organic bases. In addition, when the compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound of the formula I may be formed, for example, by reacting the compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in The Orange Book (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl) ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention. All acid and base salts, as well as solvates, are considered equivalent to the free forms of the corresponding compounds for purposes of the invention.

Generally, the compound of Formula I is either commercially available or can be prepared by a variety of methods well known to those skilled in the art, for example, by the methods as outlined in Scheme 1 below:

Scheme 1

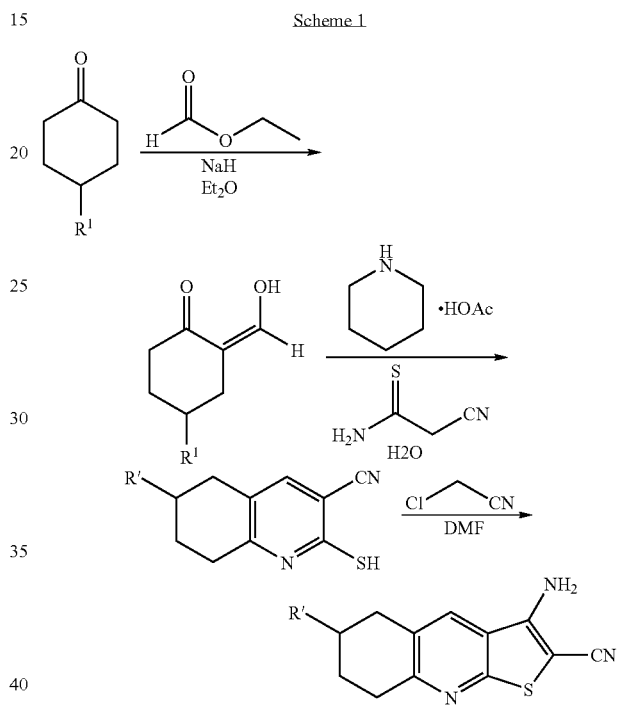

wherein $R^1$ is t-butyl.

The compound of the invention can be useful in a variety of applications involving alteration of mitosis. As will be appreciated by those skilled in the art, mitosis may be altered in a variety of ways; that is, one can affect mitosis either by increasing or decreasing the activity of a component in the mitotic pathway. Mitosis may be affected (e.g., disrupted) by disturbing equilibrium, either by inhibiting or activating certain components. Similar approaches may be used to alter meiosis.

In a particular embodiment, the compound of the invention can be used to inhibit mitotic spindle formation, thus causing prolonged cell cycle arrest in mitosis. By "inhibit" in this context is meant decreasing or interfering with mitotic spindle formation or causing mitotic spindle dysfunction. By "mitotic spindle formation" herein is meant organization of microtubules into bipolar structures by mitotic kinesins. By "mitotic spindle dysfunction" herein is meant mitotic arrest and monopolar spindle formation.

The compound of the invention is useful for binding to, and/or inhibiting the activity of, a mitotic kinesin, KSP. In one embodiment, the KSP is human KSP, although the compounds may be used to bind to or inhibit the activity of KSP kinesins from other organisms. In this context, "inhibit"

means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP (see U.S. Pat. No. 6,437,115). In addition, the present inventive compound is useful for binding to or modulating other mitotic kinesins.

The compound of the invention can be used to treat cellular proliferation diseases. Such disease states which can be treated by the compound, compositions and methods provided herein include, but are not limited to, cancer (further discussed below), hyperplasia, cardiac hypertrophy, autoimmune diseases, fungal disorders, arthritis, graft rejection, inflammatory bowel disease, immune disorders, inflammation, cellular proliferation induced after medical procedures, including, but not limited to, surgery, angioplasty, and the like. Treatment includes inhibiting cellular proliferation. It is appreciated that in some cases the cells may not be in a hyper- or hypoproliferation state (abnormal state) and still require treatment. For example, during wound healing, the cells may be proliferating "normally", but proliferation enhancement may be desired. Thus, in one embodiment, the invention herein includes application to cells or subjects afflicted or subject to impending affliction with any one of these disorders or states.

The compound, compositions and methods provided herein can be particularly useful for the treatment of cancer including solid tumors such as skin, breast, brain, colon, gall bladder, thyroid, cervical carcinomas, testicular carcinomas, etc. More particularly, cancers that may be treated by the compounds, compositions and methods of the invention include, but are not limited to:

Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver: hepatoma (hepatocellular carcinoma), cholangiocarcinoma, hepatoblastoma, angiosarcoma, hepatocellular adenoma, hemangioma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic: blood (myeloid leukemia (acute and chronic), acute lymphoblastic leukemia, acute and chronic lymphocytic leukemia, myeloproliferative diseases, multiple myeloma, myelodysplastic syndrome), Hodgkin's disease, non-Hodgkin's lymphoma (malignant lymphoma), B-cell lymphoma, T-cell lymphoma, hairy cell lymphoma, Burkeft's lymphoma, promyelocytic leukemia;

Skin: malignant melanoma, basal cell carcinoma, squamous cell carcinoma, Karposi's sarcoma, moles dysplastic nevi, lipoma, angioma, dermatofibroma, keloids, psoriasis;

Adrenal glands: neuroblastoma; and

Other tumors: including xenoderoma pigmentosum, keratoctanthoma and thyroid follicular cancer.

As used herein, treatment of cancer includes treatment of cancerous cells, including cells afflicted by any one of the above-identified conditions.

The compound of the present invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

The compound of the present invention may also be useful in inhibiting tumor angiogenesis and metastasis.

The compound of the present invention may also be useful as antifungal agents, by modulating the activity of the fungal members of the bimC kinesin subgroup, as is described in U.S. Pat. No. 6,284,480.

The present compound can also be used in combination with other known therapeutic agents and anti-cancer agents. Combinations of the present inventive compound with one or more other anti-cancer or chemotherapeutic agents are within the scope of the invention. Examples of such other anti-cancer or chemotherapeutic agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The present compound can also be useful when co-administered with radiation therapy.

The phrase "estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-ydrazone, aid SH646.

The phrase "androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

The phrase "retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, a difluoromethylornithine, ILX23-7553, trans-N-(4'-hydroxyphenyl) retinamide, and N-4-carboxyphenyl retinamide.

The phrase "cytotoxic/cytostatic agents" refer to compounds which cause cell death or inhibit cell proliferation primarily by interfering directly with the cell's functioning or inhibit or interfere with cell mycosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, monoclonal antibody therapeutics, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide (TEMODAR™ from Schering-Plough Corporation, Kenilworth, N.J.), cyclophosphamide, heptaplatin, estramustine, improsulfan tosilate, trofosfamide, nimustine, dibrospidium chloride, pumitepa, lobaplatin, satraplatin, profiromycin, cisplatin, doxorubicin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine (chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deansino-3'-morpholino-13-deoxo-10-hydroxycarminomycin, annamycin, galarubicin, elinafide, MEN10755, 4-demethoxy-3-deamino-3-aziridinyl-4-methylsulphonyl-daunombicin (see WO 00/50032), methoxtrexate, gemcitabine.

An example of a hypoxia activatable compound is tirapazamine.

Examples of proteasome inhibitors include, but are not limited to, lactacystin and bortezomib.

Examples of microtubule inhibitors/microtubule-stabilising agents include paclitaxel, vindesine sulfate, 3',4'-didehydro-4'-deoxy-8'-norvincaleukoblastine, docetaxel, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2-(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, dimesna, and camptostar.

Other useful anti-cancer agents that can be used in combination with the present compound include thymidilate synthase inhibitors, such as 5-fluorouracil.

In one embodiment, inhibitors of mitotic kinesins include, but are not limited to, inhibitors of KSP, inhibitors of MKLP1, inhibitors of CENP-E, inhibitors of MCAK, inhibitors of Kif14, inhibitors of Mphosph1 and inhibitors of Rab6-KIFL.

The phrase "inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

The phrase "antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar®.

Examples of monoclonal antibody therapeutics useful for treating cancer include Erbitux® (Cetuximab).

The phrase "HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180, 589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open acid and lactone forms is included in the scope of this invention.

The phrase "prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589, 485, 5,602,098, European Patent Publ. 0 618 221, European Patent Publ. 0 675 112, European Patent Publ. 0 604181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO, 97/30053, WO 97/44350, WO 98/02436, and U.S. Pat. No. 5,532,359. For an example of the role of a prenyl-protein transferase inhibitor on angiogenesis see *European of Cancer*, Vol. 35, No. 9, pp. 1394-1401 (1999).

Examples of farnesyl protein transferase inhibitors include SARASAR™(4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.).

The phrase "angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α (for example Intron and Peg-Intron), interleukin-12, pentosan polysulfate, cyclooxygenase inhibitors, including nonsteroidal anti-inflammatories (NSAIDS) like aspirin and ibuprofen as well as selective cyclooxygenase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin. Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compound of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). Examples of TAFIa inhibitors have been described in PCT Publication WO 03/013,526.

The phrase "agents that interfere with cell cycle checkpoints" refers to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

The phrase "inhibitors of cell proliferation and survival signaling pathway" refers to agents that inhibit cell surface receptors and signal transduction cascades downstream of those surface receptors. Such agents include inhibitors of EGFR (for example gefitinib and erlotinib), antibodies to EGFR (for example C225), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEEK (for example CI-1040 and PD-098059), inhibitors of mTOR (for example Wyeth CCI-779), and inhibitors of C-abl kinase (for example GLEEVEC™, Novartis Pharmaceuticals). Such agents include small molecule inhibitor compounds and antibody antagonists.

The phrase "apoptosis inducing agents" includes activators of TNF receptor family members (including the TRAIL receptors).

The invention also encompasses combinations of the present compound with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of IC50 for COX-2 over IC50 for COX-1 evaluated by cell or microsomal assays. Inhibitors of COX-2 that are particularly useful in the instant method of treatment are: 3-phenyl-4-(4-(methylsulfonyl) phenyl)-2-(5H)-furanone; and 5-chloro-3-(4-methylsulfonyl)phenyl-2-(2-methyl-5 pyridinyl)pyridine; or a pharmaceutically acceptable salt thereof.

Compounds that have been described as specific inhibitors of COX-2 and are therefore useful in the present invention include, but are not limited to, parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some examples of tyrosine kinase inhibitors include N-(trifluoromethylphenyl)-5-methylisoxazol-4-carboxamide, 3-[(2,4-dimethylpyrrol-5yl)methylidenyl)indolin-2-one, 17-(allylamino)-17-demethoxygeldanamycin, 4-(3-chloro-4-fluorophenylamino)-7-methoxy-6-[3-(4-morpholinyl) propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1phthalazinamine, and EMD121974.

Combinations with one or more compounds that are other than anti-cancer compounds are also encompassed in the instant methods. For example, combinations of the present compound with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999;274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid, and 2(R)-7-(3-(2-chloro-4-(4-fluorophenoxy) phenoxy)propoxy)-2-ethylchromane-2-carboxylic acid.

In one embodiment, useful anti-cancer (also known as anti-neoplastic) agents that can be used in combination with the present compound include, but are not limited, to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, doxorubicin (adriamycin), cyclophosphamide (cytoxan), gemcitabine, interferons, pegylated interferons, Erbitux and mixtures thereof.

Another embodiment of the present invention is the use of the present compound in combination with gene therapy for the treatment of cancer. For an overview of genetic strategies to treating cancer, see Hall et al (*Am J Hum Genet* 61:785-789,1997) and Kufe et al (*Cancer Medicine,* 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998;5(8):1105-13), and interferon gamma (*J Immunol* 2000; 164:217-222).

The present compound can also be administered in combination with one or more inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

The present compound can also be employed in conjunction with one or more anti-emetic agents to treat nausea or emesis, including acute, delayed, late-phase, and anticipatory emesis, which may result from the use of a compound of the present invention, alone or with radiation therapy. For the prevention or treatment of emesis, the compound of the present invention may be used in conjunction with other anti-emetic agents, especially neurokinin-1 receptor antagonists, 5HT3 receptor, antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or those as described in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In one embodiment, an anti-emesis agent selected from a neurokinin-1 receptor antagonist, a 5HT3 receptor antagonist and a corticosteroid is administered as an adjuvant for the treatment or prevention of emesis that may result upon administration of the present compounds.

Examples of neurokinin-1 receptor antagonists that can be used in conjunction with the present compound are described in U.S. Pat. Nos. 5,162,339, 5,232,929, 5,242,930, 5,373,003, 5,387,595, 5,459,270, 5,494,926, 5,496,833, 5,637,699, and 5,719,147, content of which are incorporated herein by reference. In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

The compound of the present invention may also be administered with an immunologic-enhancing drug, such as levamisole, isoprinosine and Zadaxin.

Thus, the present invention encompasses the use of the present inventive compound (for example, for treating or preventing cellular proliferative diseases) in combination with a second compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an inhibitor of inherent multidrug resistance, an anti-emetic agent, an immunologic-enhancing drug, an inhibitor of cell proliferation and survival signaling, an agent that interferes with a cell cycle checkpoint, and an apoptosis inducing agent.

In one embodiment, the present invention empassesses the composition and use of the present compound in combination with a second compound selected from: a cytostatic agent, a cytotoxic agent, taxanes, a topoisomerase II inhibitor, a topoisomerase I inhibitor, a tubulin interacting agent, hormonal agent, a thymidilate synthase inhibitors, anti-metabolites, an alkylating agent, a farnesyl protein transferase inhibitor, a signal transduction inhibitor, an EGFR kinase inhibitor, an antibody to EGFR, a C-abl kinase inhibitor, hormonal therapy combinations, and aromatase combinations.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In one embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MW (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-(O-chloroacetylcarbonyl)-fumagillol, thalidomide, angiostatin, troponin-1, or an antibody to VEGF. In an embodiment, the estrogen receptor modulator is tamoxifen or raloxifene.

Also included in the present invention is a method of treating cancer comprising administering a therapeutically effective amount of the compound of Formula I in combination with radiation therapy and at least one compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an inhibitor of inherent multidrug resistance, an anti-emetic agent, an immunologic-enhancing drag, an inhibitor of cell proliferation and survival signaling, an agent that interferes with a cell cycle checkpoint, and an apoptosis inducing agent.

Yet another embodiment of the invention is a method of treating cancer comprising administering a therapeutically effective amount of the compound of Formula I in combination with paclitaxel or trastuzumab.

The present invention also includes a pharmaceutical composition useful for treating or preventing cellular proliferation diseases (such as cancer, hyperplasia, cardiac hypertrophy, autoimmune diseases, fungal disorders, arthritis, graft rejection, inflammatory bowel disease, immune disorders, inflammation, and cellular proliferation induced after medical procedures) that comprises a therapeutically effective amount of the compound of Formula I and at least one compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an inhibitor of cell proliferation and survival signaling, an agent that interferes with a cell cycle checkpoint, and an apoptosis inducing agent.

Another aspect of this invention relates to a method of selectively inhibiting KSP kinesin activity in a subject (such as a cell, animal or human) in need thereof, comprising contacting said subject with the compound of Formula I or a pharmaceutically acceptable salt or solvate thereof.

Another aspect of this invention relates to a method of treating or preventing a disease or condition associated with KSP in a subject (e.g., human) in need thereof comprising administering a therapeutically effective amount of the compound of Formula I or a pharmaceutically acceptable salt or solvate thereof to said subject.

A preferred dosage is about 0.001 to 500 mg/kg of body weight/day of the compound of Formula I or a pharmaceutically acceptable salt or solvate thereof. An especially preferred dosage is about 0.01 to 25 mg/kg of body weight/day of the compound of Formula I or a pharmaceutically acceptable salt or solvate thereof.

The phrases "effective amount" and "therapeutically effective amount" mean that amount of the compound of Formula I, and other pharmacological or therapeutic agents described herein, that will elicit a biological or medical response of a tissue, a system, or a subject (e.g., animal or human) that is being sought by the administrator (such as a researcher, doctor or veterinarian) which includes alleviation of the symptoms of the condition or disease being treated and the prevention, slowing or halting of progression of one or more cellular proliferation diseases. The formulations or compositions, combinations and treatments of the present invention can be administered by any suitable means which produce contact of these compounds with the site of action in the body of, for example, a mammal or human.

For administration of pharmaceutically acceptable salts of the above compounds, the weights indicated above refer to the weight of the acid equivalent or the base equivalent of the therapeutic compound derived from the salt.

As described above, this invention includes combinations comprising an amount of the compound of Formula I or a pharmaceutically acceptable salt or solvate thereof, and an amount of one or more additional therapeutic agents listed above (administered together or sequentially) wherein the amounts of the compounds/treatments result in desired therapeutic effect.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for illustration purposes, the compound of Formula I and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

If formulated as a fixed dose, such combination products employ the compounds of this invention within the dosage range described herein and the other pharmaceutically active agent or treatment within its dosage range. The compound of Formula I may also be administered sequentially with known therapeutic agents when a combination formulation is inappropriate. The invention is not limited in the sequence of administration; the compound of Formula I may be administered either prior to or after administration of the known therapeutic agent. Such techniques are within the skills of persons skilled in the art as well as attending physicians.

The pharmacological properties of the compound of this invention may be confirmed by a number of pharmacological assays. The inhibitory activity of the present compounds towards KSP may be assayed by methods known in the art, for example, by using the methods as described below.

While it is possible for the active ingredient to be administered alone, it is preferable to present it as a pharmaceutical composition. The compositions of the present invention comprise at least one active ingredient, as defined above, together with one or more acceptable carriers, adjuvants or vehicles thereof and optionally other therapeutic agents. Each carrier, adjuvant or vehicle must be acceptable in the sense of being compatible with the other ingredients of the composition and not injurious to the mammal in need of treatment.

Accordingly, this invention also relates to pharmaceutical compositions comprising the compound of Formula I, or a pharmaceutically acceptable salt or solvate thereof and at least one pharmaceutically acceptable carrier, adjuvant or vehicle.

For preparing pharmaceutical compositions from the compound described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

The term pharmaceutical composition is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a subject by administering a pharmaceutical composition of the present invention is also intended to encompass the administration of the afore-said bulk composition and individual dosage units.

Additionally, the compositions of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts or solvates thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of the compound of Formula I or a pharmaceutically acceptable salt or solvate thereof and at least one pharmaceutically acceptable carrier, adjuvant or vehicle.

Yet another aspect of this invention is a kit comprising an amount of the compound of Formula I or a pharmaceutically acceptable salt or solvate thereof and an amount of at least one additional therapeutic agent listed above, wherein the amounts of the two or more ingredients result in desired therapeutic effect.

The KSP inhibitory activity of the compound of Formula I was measured by the following assays.

KSP Assays:

Endpoint Assay:

Serial dilutions of the compounds were prepared in a low binding, 96-well microtiter plate (Costar # 3600) using 40% DMSO (Fisher BP231). The diluted compounds were added to a 384-well microtiter plate (Fisher 12-565-506). The following was then added to each well of the 384 microtiter plate: 55 µg/mL purified microtubules (Cytoskeleton TL238), 2.5-10 nM KSP motor domain [made according to Hopkins et al, *Biochemistry*, (2000) 39, 2805-2814)], 20 mM ACES pH 7.0 (Sigma A-7949), 1 mM EGTA (Sigma E-3889), 1 mM $MgCl_2$ (Sigma M-2670), 25 mM KCl (Sigma P-9333), 10 µM paclitaxel (Cytoskeleton TXD01), and 1 mM DTT (Sigma D5545) [final concentration]. Following a 10 minute incubation, ATP (Sigma A-3377) (final concentration of ATP: 100 µM) was added to start the reaction. The final reaction volume was 25 µL. Final test compound concentration ranged from 50 µM to 5 nM. The reaction was incubated for 1 hour at room temperature. The reaction was stopped by the addition of 50 µL Biomol green reagent (Biomol AK111) per well, and was allowed to incubate for 20 minutes at room temperature. The 384-well microtiter plate was then transferred to an absorbance reader (Molecular Devices SpectraMax plus) and a single measurement was taken at 620 nm.

Kinetic Assay:

Compound dilutions were prepared as described previously. 25A25 buffer consisted of the following: 25 mM ACES pH 6.9, 2 mM MgOAc (Sigma M-9147), 2 mM EGTA, 0.1 mM EDTA (Gibco 144475-038), 25 mM KCl, 1 mM 2-mercaptoethanol (Biorad 161-0710), 10 µM paclitaxel, and 0.5 mM DTT. Solution 1 consisted of the following: 3.75 mM [final concentration] phosphoenol pyruvic acid (PEP, 2.5×) (Sigma P-7127), 0.75 mM MgATP (2.5×) (Sigma A-9187) in 1×25A25 buffer. Solution 2 consisted of the following: 100-500 nM KSP motor domain (2×), 6 U/mL pyruvate kinase/lactate dehydrogenase (2×) (Sigma P-0294), 110 µg/mL purified microtubules (2×), 1.6 µM β-nicotinamide adenine di-nucleotide, reduced form (NADH, 2×) (Sigma N-8129) in 1×25A25 buffer. Compound dilutions [8] were added to a 96-well microtiter plate (Costar 9018), and 40 µL of solution 1 was added to each well. The reaction was started by adding 50 µL of solution 2 to each well. The respective final assay concentrations were: 1.5 mM PEP, 0.3 mM MgATP, 50-250 nM KSP motor domain, 3 U/mL pyruvate kinase/lactate dehydrogenase, 55 µg/mL purified microtubules, 0.8 µM NADH [final concentrate]. The microtiter plate was then transferred to an absorbance reader and multiple readings were taken for each well in a kinetic mode at 340 nm [25 measurements for each well approcimately every 12 seconds, spread approximately over about 5 minutes time span]. For each reaction, a rate of change was determined.

Calculations:

For both endpoint and kinetic assays, the percent activity for each concentration is calculated using the following equation:

$$Y = ((X - \text{background})/(\text{positive control} - \text{background})) * 100$$

Y is the % activity and X is the measured reading (OD620 or rate)

For an $IC_{50}$ determination, the % activity was fit by the following equation using a nonlinear curve-fitting program for sigmoidal dose-responses (variable slopes) (GraphPad Prizm).

$$Y = \text{Bottom} + (\text{Top} - \text{Bottom})/(1 + 10^{\wedge}((\text{Log}EC50 - X)*\text{HillSlope}))$$

X is the logarithm of concentration. Y is the response.
Y starts at Bottom and goes to Top with a sigmoid shape.

REFERENCES

KSP/Kinesin as Target
1) Blangy, A et al. (1995) Cell 83, 1159-1169 (cloning of human KSP, function in mitosis).
2) Sawin, K. and Mitchison, T. J. (1995) Proc. Natl. Acad. Sci. 92, 4289-4293 (*Xenopus* Egd5, conserved motor domain, function).
3) Huang, T.-G. and Hackney, D. D. (1994) J. Biol. Chem. 269, 16493-16501 (Drosphila kinesin minimal motor domain definition, expression and purification from *E. coli*).
4) Kaiser A. et al. (1999) J. Biol. Chem. 274, 18925-18931 (overexpression of KSP motor domain, function in mitosis, inhibition of growth by targeting KSP).
5) Kapoor T. M and Mitchison, T. J. (1999) Proc. Natl. Acad. Sci. 96, 9106-9111 (use of KSP motor domain, inhibitors thereof.
6) Mayer, T. U. (1999) Science 286, 971-974 (KSP inhibitors as anticancer drugs).

KSP Assays (Endpoint and Kinetics)
7) Wohlke, G. et al. (1997) Cell 90, 207-216 (expression and purification of kinesin motor domain, kinetics assay, endpoint assay).
8) Geladeopoulos, T. P. et al. (1991) Anal. Biochem. 192, 112-116 (basis for endpoint assay).
9) Sakowicz, R. et al. (1998) Science 280, 292-295 (kinetics assay).
10) Hopkins, S. C. et al. (2000) Biochemistry 39, 2805-2814 (endpoint and kinetics assay).
11) Maliga, Z. et al. (2002) Chem. & Biol. 9, 989-996 (kinetics assay).

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Therefore, we claim:

1. A pharmaceutical composition comprising a therapeutically effective amount of a compound of Formula I or a pharmaceutically acceptable salt thereof, in combination with a pharmaceutically acceptable carrier, adjuvant or vehicle:

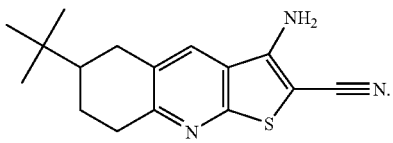

2. The composition of claim 1, wherein the compound is the (+)-enantiomer of

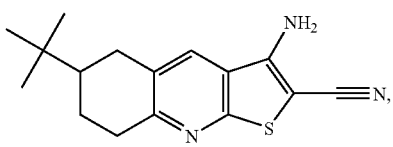

or a pharmaceutically acceptable salt thereof.

3. The composition of claim 1, wherein the compound is the (−)-enantiomer of

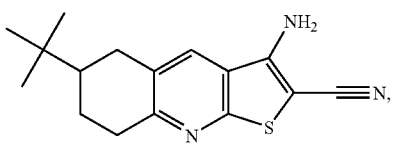

or a pharmaceutically acceptable salt thereof.

4. The pharmaceutical composition of claim 1, further comprising one or more compounds selected from the group consisting of an anti-cancer agent, a PPAR-γ agonist, a PPAR-δ agonist, an inhibitor of inherent multidrug resistance, an anti-emetic agent, and an immunologic-enhancing drug.

5. The pharmaceutical composition of claim 4, wherein the anti-cancer agent is selected from the group consisting of an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, an inhibitor of cell proliferation and survival signaling, an agent that interferes with a cell cycle checkpoint, and an apoptosis inducing agent.

6. The pharmaceutical composition of claim 4, further comprising one or more anti-cancer agents selected from the group consisting of cytostatic agents, cytotoxic agents, taxanes, topoisomerase II inhibitors, topoisomerase I inhibitors, tubulin interacting agents, hormonal agents, thymidilate synthase inhibitors, anti-metabolites, alkylating agents, farnesyl protein transferase inhibitors, signal transduction inhibitors, EGER kinase inhibitors, antibodies to EGER, C-abl kinase inhibitors, hormonal therapy combinations, and aromatase combinations.

7. The pharmaceutical composition of claim 4, further comprising one or more agents selected from the group consisting of Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methyiprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethyl melamine, doxorubicin, cyclophosphamide, gemcitabine, interferons, pegylated interferons, Erbitux and mixtures thereof.

* * * * *

UNITED STATES PATENT AND TRADEMARK OFFICE
CERTIFICATE OF CORRECTION

| | | |
|---|---|---|
| PATENT NO. | : 7,608,643 B2 | Page 1 of 1 |
| APPLICATION NO. | : 11/370005 | |
| DATED | : October 27, 2009 | |
| INVENTOR(S) | : Ronald J. Doll et al. | |

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 337 days.

Claim 6, column 22, line 26, delete $1^{st}$ & $6^{th}$ word "EGER" and insert --EGFR-- in both places.

Claim 7, column 22, line 43, delete "Methyipred" and insert --Methylpred--.

Signed and Sealed this

Twenty-fourth Day of August, 2010

David J. Kappos
*Director of the United States Patent and Trademark Office*